United States Patent
Kulkarni et al.

(10) Patent No.: US 10,046,163 B2
(45) Date of Patent: *Aug. 14, 2018

(54) CONNECTORIZED COCHLEAR IMPLANT SYSTEMS

(71) Applicant: ADVANCED BIONICS AG, Staefa (CH)

(72) Inventors: Abhijit Kulkarni, Newbury Park, CA (US); Wantjinarjo Suwito, Longmont, CO (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,662

(22) Filed: Nov. 29, 2017

(65) Prior Publication Data
US 2018/0078765 A1 Mar. 22, 2018

Related U.S. Application Data

(63) Continuation of application No. 14/909,972, filed as application No. PCT/US2013/055351 on Aug. 16, 2013, now Pat. No. 9,861,819.

(51) Int. Cl.
*A61N 1/36* (2006.01)
*A61N 1/372* (2006.01)
(Continued)

(52) U.S. Cl.
CPC ......... *A61N 1/36036* (2017.08); *A61N 1/375* (2013.01); *A61N 1/3787* (2013.01);
(Continued)

(58) Field of Classification Search
CPC .. A61N 1/36032; A61N 1/3723; A61N 1/375; A61N 1/3787
See application file for complete search history.

(56) References Cited

U.S. PATENT DOCUMENTS 6,272,382 B1 8/2001 Faltys et al.
6,308,101 B1 10/2001 Faltys et al.
(Continued)

FOREIGN PATENT DOCUMENTS

CN 101969596 2/2011
EP 2293600 3/2011
(Continued)

OTHER PUBLICATIONS

Communication pursuant to Article 94(3) EPC received in European Patent Application No. 13753756.9, dated Jun. 20, 2017.
(Continued)

*Primary Examiner* — Joseph Dietrich
(74) *Attorney, Agent, or Firm* — ALG Intellectual Property, LLC

(57) ABSTRACT

An exemplary system includes 1) a cochlear implant module configured to be implanted within a patient and including cochlear implant circuitry configured to apply electrical stimulation representative of one or more audio signals to the patient, 2) a first connector assembly coupled to the cochlear implant module and configured to be implanted within the patient, the first connector assembly including a first set of induction coils, 3) an implantable module configured to be implanted within the patient, and 4) a second connector assembly coupled to the implantable module and configured to be implanted within the patient, the second connector assembly including a second set of induction coils. The first and second sets of induction coils are configured to form a multi-channel inductive link between the implantable module and the cochlear implant module. Corresponding systems are also disclosed.

20 Claims, 9 Drawing Sheets

(51) Int. Cl.
    H04B 5/00        (2006.01)
    A61N 1/378       (2006.01)
    A61N 1/375       (2006.01)
(52) U.S. Cl.
    CPC ....... *A61N 1/37223* (2013.01); *H04B 5/0006* (2013.01); *H04B 5/0037* (2013.01); *H04B 5/0075* (2013.01); *H04B 5/0093* (2013.01)

(56) References Cited

U.S. PATENT DOCUMENTS

| | | |
|---|---|---|
| 2002/0154518 A1 | 10/2002 | Elferich et al. |
| 2006/0122664 A1 | 6/2006 | Sacha et al. |
| 2006/0183965 A1 | 8/2006 | Kasic, II et al. |
| 2012/0109256 A1 | 5/2012 | Meskins et al. |
| 2012/0116479 A1 | 5/2012 | Meskins et al. |

FOREIGN PATENT DOCUMENTS

| | | |
|---|---|---|
| WO | 2006089047 | 8/2006 |
| WO | 2009/056167 | 5/2009 |
| WO | 2010/028436 | 3/2010 |
| WO | 2012/063202 | 5/2012 |

OTHER PUBLICATIONS

Final Office Action received in U.S. Appl. No. 14/909,972 dated Jun. 16, 2017.
First Office Action received in Chinese Patent Application No. 201380078922.8, dated Mar. 10, 2017.
International Search Report and Written Opinion received in International Application No. PCT/US13/055351, dated Nov. 28, 2013.
Non-Final Office Action received in U.S. Appl. No. 14/909,972 dated Jan. 5, 2017.
Second Office Action received in Chinese Patent Application No. 201380078922.8, dated Aug. 15, 2017.

CONNECTORIZED COCHLEAR IMPLANT SYSTEMS

RELATED APPLICATIONS

The present application is a continuation application of U.S. patent application Ser. No. 14/909,972, filed Feb. 3, 2016, which application is a U.S. National Stage Entry of PCT Application No. PCT/US13/55351, filed Aug. 16, 2013. The contents of these applications are incorporated herein by reference in their respective entireties.

BACKGROUND INFORMATION

Conventional cochlear implant systems include various components configured to be implanted within a patient (e.g., a cochlear implant, an antenna, and an electrode lead) and various components configured to be located external to the patient (e.g., a sound processor, a battery, and a microphone). Unfortunately, the external components of a conventional cochlear implant system are often relatively large, bulky, and aesthetically unpleasing. Hence, various partially and fully implantable cochlear implant systems have been described in which the sound processor and/or one or more other components typically located external to the patient (i.e., the battery and/or the microphone) are also implanted within the patient. In these configurations, the patient may enjoy cochlear implant functionality with little or no externally located components for various periods throughout the day.

Unfortunately, certain implanted components, such as a battery, need to be replaced periodically to ensure proper functionality of the cochlear implant system. Such periodic replacement of one or more implanted components would typically require a patient to undergo a surgical procedure in which all of the already implanted components of the conventional cochlear implant system are replaced with the new fully implantable cochlear implant system components. In addition to being invasive and costly, this surgical procedure could potentially cause damage to one or more of the patient's auditory structures and thereby negate any benefits that could be provided by the fully implantable cochlear implant system.

Certain implantable systems (e.g., cardiac rhythm management and pain management systems) provide for replacement of implantable batteries by utilizing modular connectors to connect the implantable batteries to other system components. Such modular connectors transfer power from an implantable battery to other system components via a direct galvanic connection between separate metal contacts. While such connectors allow for removal and replacement of an implantable battery independent of other implantable components, there exists a potential for moisture from an internal patient environment to come in contact with the metal contacts of the connectors. Moisture contacting the metal contacts of the connectors can compromise the direct connection between the connector components, thereby reducing or eliminating the transfer of power from the implantable battery to the rest of the implantable system. Moreover, moisture contacting the metal contacts of the connector may present a hazard to the patient, as current may leak into the internal patient environment causing irritation and/or damage to sensitive tissues and organs.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
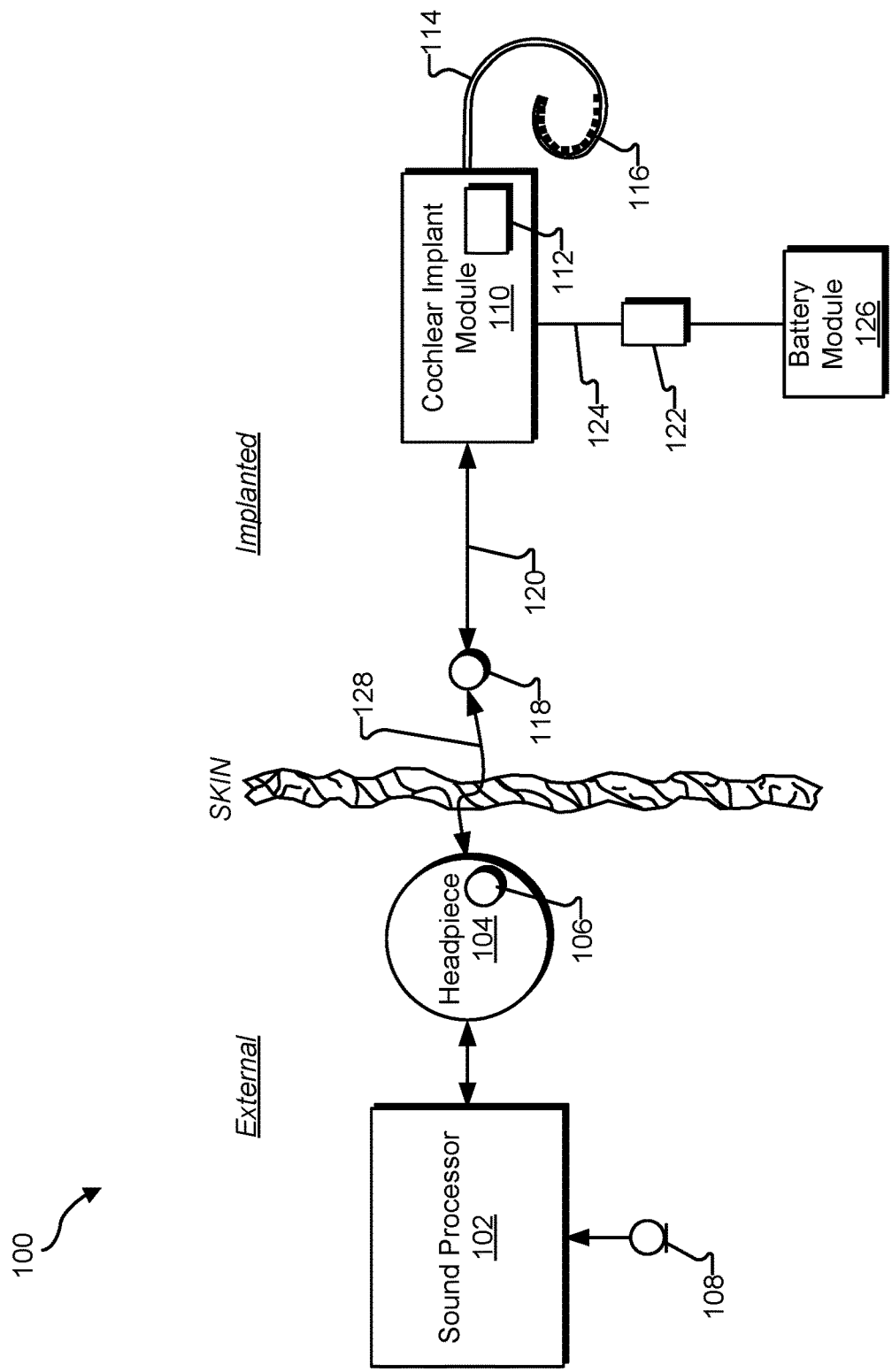
FIG. 1 illustrates an exemplary connectorized cochlear implant system according to principles described herein.

Connectorized cochlear implant systems and methods are described herein. As will be described in more detail below, a connectorized cochlear implant system may include 1) a cochlear implant module configured to be implanted within a patient and comprising cochlear implant circuitry configured to apply electrical stimulation representative of one or more audio signals to the patient, 2) a first connector assembly coupled to the cochlear implant module and configured to be implanted within the patient, the first connector assembly comprising a first induction coil, 3) an implantable module (e.g., an implantable battery module or an implantable module that includes a sound processor and a battery) configured to be implanted within the patient, and 4) a second connector assembly coupled to the implantable module and configured to be implanted within the patient, the second connector assembly comprising a second induction coil. The first connector assembly may be configured to be removably connected to the second connector assembly in order to facilitate inductive transfer of power between the first induction coil and the second induction coil. In this configuration, power may be inductively transmitted from the first connector assembly to the second connector assembly without direct contact between metal components of the first connector assembly and the second connector assembly. Indeed, electrically conductive components of each of the first connector assembly and the second connector assembly may be hermetically sealed so as to prevent direct contact between the internal patient environment and any electrically conductive portions of the first connector assembly and the second connector assembly.

The systems and methods described herein may facilitate individual replacement of one or more components of a cochlear implant system after they have been implanted within a patient. For example, a patient may be fitted with a connectorized cochlear implant system such as those described herein. The connector assemblies included in the connectorized cochlear implant system may be connected to an implantable module, such as an implantable battery or a module containing both a sound processor and an implantable battery. Following initial implantation, an implantable battery may subsequently require replacement as part of a service schedule or due to failure of the battery. To replace the implantable battery, the patient may undergo a minimally invasive surgical procedure during which the implantable battery is disconnected from the modular connector, discarded, and replaced with a new implantable battery (e.g., by connecting the first connector assembly coupled to a cochlear implant module to a second connector assembly coupled to the implantable battery.) Advantageously, the remaining implanted components (i.e., the cochlear implant module and the electrode lead) may be left intact, thereby preserving their functionality and avoiding the cost and potential dangers associated with replacing them with new components as well.

FIG. 1 illustrates an exemplary connectorized cochlear implant system 100. As shown, connectorized cochlear implant system 100 may include various components configured to be located external to a patient including, but not limited to, a sound processor 102, a headpiece 104, an external antenna 106, and a microphone 108. Connectorized cochlear implant system 100 may further include various components configured to be implanted within the patient including, but not limited to, a cochlear implant module 110, cochlear implant circuitry 112 included within cochlear implant module 110, a lead 114 having a plurality of electrodes 116 disposed thereon, an implantable antenna 118 connected to cochlear implant module 110 via a cable 120, a connector junction 122 disposed at a distal end of a cable 124 coupled to cochlear implant module 110, and an implantable battery module 126 coupled to connector junction 122. As will be described in more detail below, additional or alternative components may be included within connectorized cochlear implant system 100 as may serve a particular implementation. The components shown in FIG. 1 will now be described in more detail.

Sound processor 102 may be configured to direct cochlear implant circuitry 112 to generate and apply electrical stimulation (also referred to herein as "stimulation current") representative of one or more audio signals (e.g., one or more audio signals detected by microphone 108, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 102 may process the one or more audio signals in accordance with a selected sound processing strategy or program to generate appropriate stimulation parameters for controlling cochlear implant circuitry 112. Sound processor 102 may include or be implemented by a behind-the-ear ("BTE") unit, a body worn device, an electro-acoustic stimulation ("EAS") device, and/or any other sound processing unit as may serve a particular implementation.

Headpiece 104 may be communicatively coupled to sound processor 102 and may include an external antenna 106 (e.g., a coil and/or one or more wireless communication components) configured to facilitate selective wireless coupling of sound processor 102 to cochlear implant circuitry 112. Headpiece 104 may be additionally or alternatively used to selectively and wirelessly couple any other external device to cochlear implant circuitry 112. To this end, headpiece 104 may be configured to be affixed to the patient's head and positioned such that external antenna 106 is communicatively coupled to implantable antenna 118 (which may also be implemented by a coil and/or one or more wireless communication components). In this manner, stimulation parameters and/or power signals (in the event of battery module 126 failure) may be wirelessly transmitted between sound processor 102 and cochlear implant module 110 via a communication link 128 (which may include a bi-directional communication link and/or one or more dedicated uni-directional communication links as may serve a particular implementation).

Cochlear implant module 110 may be implemented by any type of implantable stimulator that may be used in association with the systems and methods described herein. For example, cochlear implant module 110 may be implemented by an implantable cochlear stimulator. In some alternative implementations, cochlear implant module 110 may be implemented by a brainstem implant and/or any other type of cochlear implant that may be implanted within a patient.

In some examples, cochlear implant module 110 may include cochlear implant circuitry 112 disposed therein. In these examples, cochlear implant module 110 may include a hermetic housing or feedthrough case configured to house cochlear implant circuitry 112. Cochlear implant circuitry 112 may be configured to generate electrical stimulation representative of an audio signal processed by sound processor 102 (e.g., an audio signal detected by microphone 108) in accordance with one or more stimulation parameters transmitted thereto by sound processor 102. Cochlear implant circuitry 112 may be further configured to apply the electrical stimulation to one or more stimulation sites within the patient via one or more electrodes 116 disposed along lead 114. In some examples, cochlear implant circuitry 112 may include a plurality of independent current sources each associated with a channel defined by one or more of electrodes 116. In this manner, different stimulation current levels may be applied to multiple stimulation sites simultaneously by way of multiple electrodes 116.

As shown, cochlear implant module 110 may be coupled to each of lead 114, cable 120, and cable 124. Lead 114, cable 120, and cable 124 may each be coupled to cochlear implant module 110 in any suitable manner. For example, a proximal end of lead 114 may be integrated into or otherwise permanently coupled to cochlear implant module 110 such that the one or more wires disposed within lead 114 and associated with electrodes 116 may pass through cochlear implant module 110 to cochlear implant circuitry 112. Likewise, a proximal end of cable 120 may be integrated into or otherwise permanently coupled to cochlear implant module 110 such that one or more wires disposed within cable 120 may pass through cochlear implant module 110 to cochlear implant circuitry 112.

As shown, implantable antenna 118 may be coupled to cochlear implant module 110 by way of cable 120. In some examples, cable 120 may include one or more wires disposed therein configured to facilitate electrical connection of one or more corresponding contacts (e.g., pins) included in implantable antenna 118 to one or more feedthrough connections included in cochlear implant circuitry 112. Alternatively, cable 120 may include one or more optical fibers and/or any other type of data transmission means as may serve a particular implementation. For purposes of the examples described herein, it will be assumed that cable 120 includes one or more wires disposed therein.

In some examples, connector junction 122 may be coupled to cochlear implant module 110 by way of cable 124. For example, connector junction 122 may be coupled to a distal end of cable 124 in any suitable manner. In some examples, connector junction 122 may be integrated into cochlear implant module 110 or otherwise associated with cochlear implant module 110. Cable 124 may include one or more wires disposed therein configured to facilitate transfer of power to cochlear implant circuitry 112. Connector junction 122 may also be associated with implantable battery module 126, integrated into implantable battery module 126, coupled to a distal end of a cable connected to implantable battery module 126, or otherwise associated with implantable battery module 126. Implantable battery module 126 may include one or more batteries configured to provide operating power for one or more other implanted components, such as cochlear implant circuitry 112. It will be recognized that any of the battery modules described herein may be rechargeable or non-rechargeable as may serve a particular implementation.

As will be described herein, connector junction 122 may include connector assemblies (e.g., first connector assembly 202 or second connector assembly 204 illustrated in FIG. 2) that are removably connected one to another. As used herein, references to connector assemblies being "removably connected" one to another refer to the connector assemblies being capable of being relatively easily and/or readily disconnected from each other by a surgeon or other person in a way that does not damage either of the connector assemblies. Implantable battery module 126 may be communicatively coupled to cochlear implant circuitry 112 while implantable battery module 126 is connected to connector junction 122.

In some examples, a connector assembly of connector junction 122 may be disconnected from implantable battery module 126 and connected to another component (e.g., a replacement battery module for implantable battery module 126, or another suitable component). Disconnection of the connector assembly from implantable battery module 126 and connection of the connector assembly to another component may be performed, e.g., by a surgeon during a surgical procedure.

Figure 2:
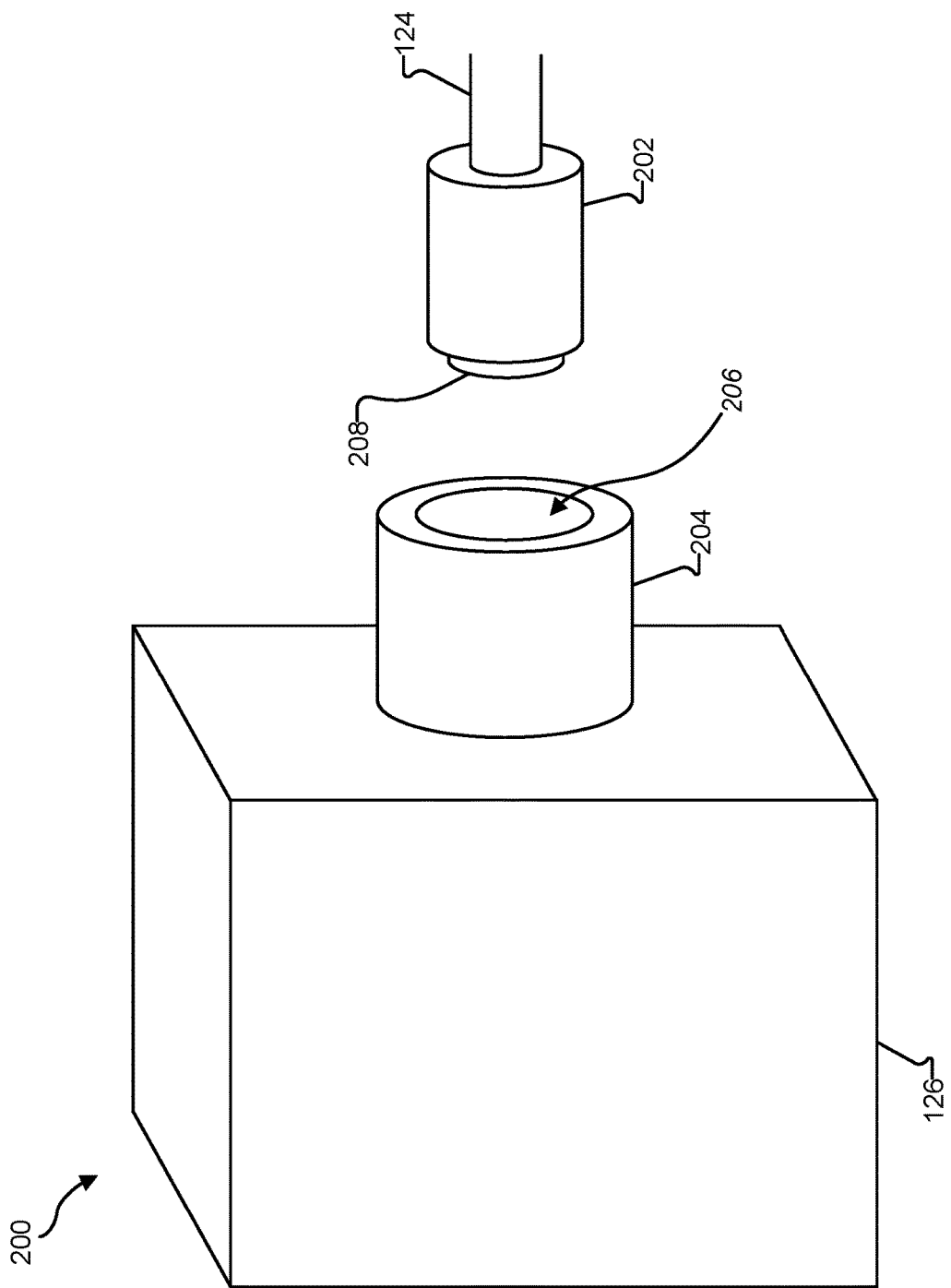
FIGS. 2-9 illustrate exemplary implementations of the connectorized cochlear implant system of FIG. 1 according to principles described herein.

FIG. 2 illustrates an exemplary configuration 200 of connectorized cochlear implant system 100 in which connector assembly components that are included within connector junction 122 of connectorized cochlear implant system 100 are shown separated. A first connector assembly 202 may be attached to a distal end of cable 124 such that first connector assembly 202 is coupled to cochlear implant module 110 by cable 124. Additionally, a second connector assembly 204 may be directly attached to implantable battery module 126. For example, second connector assembly 204 may be mounted to an exterior of battery module 126. In some embodiments, second connector assembly 204 may be disposed partially or fully within implantable battery module 126.

First connector assembly 202 and second connector assembly 204 may be configured to be coupled one to another. As shown, second connector assembly 204 may include a receptacle 206 for accommodating first connector assembly 202. For example, receptacle 206 may have a diameter configured to fit around an exterior of first connector assembly 202. Although first connector assembly 202 and second connector assembly 204 are each illustrated as having a substantially cylindrical periphery, first connector assembly 202 and second connector assembly 204 may comprise any suitable shape or configuration, without limitation.

First connector assembly 202 may include a fastening or attachment portion for securely holding first connector assembly 202 within second connector assembly 204. For example, first connector assembly 202 may comprise a magnet 208 positioned at a distal end of first connector assembly 202. Magnet 208 may be configured to be positioned adjacent a corresponding magnet within second connector assembly 204, thereby securely holding first connector assembly 202 within second connector assembly 204. In some examples, instead of utilizing a magnetic connection to hold first connector assembly 202 and second connector assembly 204 together, first connector assembly 202 and second connector assembly 204 may be mechanically fastened together using any suitable fastening mechanism.

For example, a spring-loaded locking mechanism may be utilized to secure first connector assembly 202 within second connector assembly 204. Such a spring-loaded locking mechanism may enable an individual, such as a surgeon, to readily position and secure first connector assembly 202 within second connector assembly 204 by inserting first connector assembly 202 into receptacle 206 of second connector assembly 204 and then rotating first connector assembly 202 within receptacle 206 such that a portion of first connector assembly 202 is forced against a portion of second connector assembly 204, thereby preventing detachment of first connector assembly 202 from second connector assembly 204 under normal conditions. When first connector assembly 202 is connected to second connector assembly 204, power may be inductively transferred between first connector assembly 202 and second connector assembly 204 via induction coils in the respective connector assemblies. In some examples, first connector assembly 202 may be fastened to second connector assembly 204 by a snap-type fastener having interlocking connection portions that enable first connector assembly 202 to be freely rotated within second connector assembly 204 without disconnecting first connector assembly from second connector assembly 204.

Figure 3:
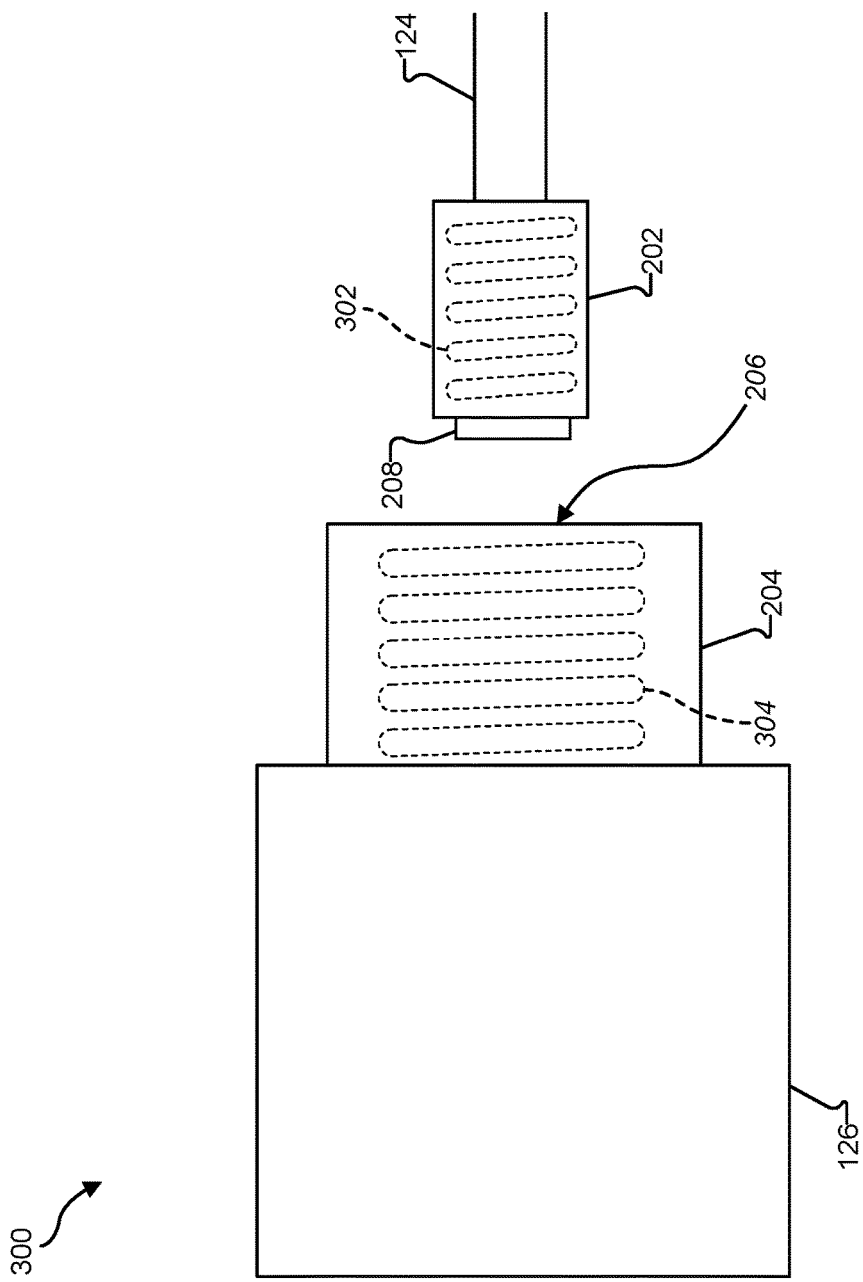

To illustrate, FIG. 3 shows an exemplary configuration 300 of connectorized cochlear implant system 100 in which first connector assembly 202 and second connector assembly 204 included within connector junction 122 of connectorized cochlear implant system 100 are shown separated. Power from implantable battery module 126 (i.e., from a battery included in implantable battery module 126) may be transferred to cochlear implant circuitry 112 of cochlear implant module 110 via inductive transfer from second connector assembly 204 to first connector assembly 202. In some examples, power may also be transferred from cochlear implant module 110 to implantable battery module 126 via inductive transfer from first connector assembly 202 to second connector assembly 204 for purposes of periodically recharging implantable battery module 126.

In order to provide for inductive transfer of power between first connector assembly 202 and second connector assembly 204, first connector assembly 202 may comprise a first induction coil 302 and second connector assembly 204 may comprise a second induction coil 304. First induction coil 302 and/or second induction coil 304 may comprise a conductive wire that is wound into a tubular configuration. In some examples, first induction coil 302 and/or second induction coil 304 may include an elongated substrate, such as a polymer substrate, that is coated with a conductive material. For example, first induction coil 302 and/or second induction coil 304 may comprise a polyimide and/or a liquid crystal polymer substrate that is coated with a conductive material layer.

First induction coil 302 and second induction coil 304 may each comprise any suitable conductive material, such as a conductive metal. First induction coil 302 may comprise, for example, titanium, gold, platinum, and/or an alloy thereof. In some examples, first induction coil 302 and/or second induction coil 304 may include an implantable high-Q coil having a relatively high Q factor (i.e., quality factor), although coils having lower Q factors may also be utilized. Additionally, first induction coil 302 may surround a core formed of a ferromagnetic material, such as a ferrite rod, that increases an inductive coupling factor between first induction coil 302 and second induction coil 304. First induction coil 302 and/or second induction coil 304 may be hermetically sealed or encased so as to prevent fluids, such as patient body fluids, from directly contacting first induction coil 302 and/or second induction coil 304. For example, first induction coil 302 and second induction coil 304 may each be encased in a resilient polymer, such as medical-grade epoxy, to seal and protect first induction coil 302 and second induction coil 304 from fluids. In some examples, a separate protective layer, such as a hermetic enclosure, may surround first induction coil 302 and/or second induction coil 304.

First induction coil 302 and second induction coil 304 may each have the same or different inductances. In some examples, first induction coil 302 and second induction coil 304 may each have the same number of turns of wire forming the respective coils such that first induction coil 302 and second induction coil 304 each have substantially the same inductance. Additionally, first induction coil 302 and second induction coil 304 may have different numbers of turns of wire, resulting in first induction coil 302 and second induction coil 304 each having different inductances. According to some examples, first induction coil 302 and second induction coil 304 may each have one or more sets of windings. For example, first induction coil 302 may have a plurality of sets of windings corresponding to a plurality of sets of windings in second coil 302, with each set of winding in first induction coil 302 being concentrically surrounded by a corresponding set of winding in second induction coil 304. In at least one example, each of the plurality of sets of windings in first induction coil 302 and/or second induction coil 304 may correspond to a separate channel, such as a power and/or data signal channel.

Figure 4:
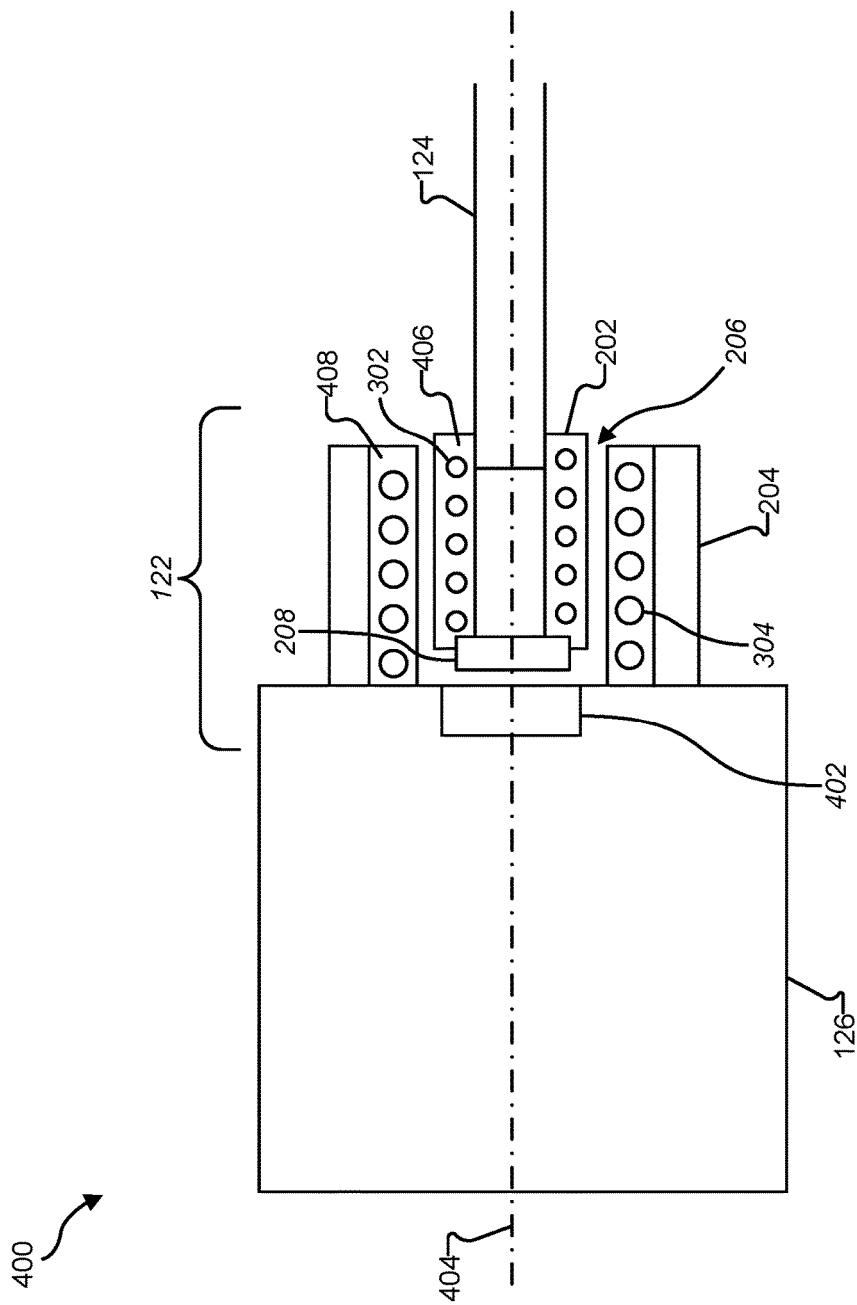

FIG. 4 illustrates an exemplary configuration 400 of connectorized cochlear implant system 100 in which first connector assembly 202 is connected to second connector assembly 204 of connector junction 122. As shown, first connector assembly 202 may be disposed within receptacle 206 of second connector assembly 204.

Magnet 208 of first connector assembly 202 may be positioned adjacent a magnet 402 of second connector assembly 204, thereby securing first connector assembly 202 to second connector assembly 204. Magnet 402 may be disposed in a portion of implantable battery module 126 near an inner portion of receptacle 206 of second connector assembly 204. In some examples, magnet 402 may be located in a portion of second connector assembly 204 near implantable battery module 126. Additionally, instead of utilizing a magnetic connection to hold first connector assembly 202 and second connector assembly 204 together, first connector assembly 202 and second connector assembly 204 may be mechanically fastened together.

According to some examples, when first connector assembly 202 and second connector assembly 204 are connected, first connector assembly 202 and second connector assembly 204 may both be oriented so as to surround an axis 404, as shown. Particularly, first induction coil 302 and second induction coil 304 may be positioned so as to surround axis 404. For example, first induction coil 302 and second induction coil 304 may each follow a helical path that is generally centered about axis 404. Second induction coil 304 may be positioned surrounding receptacle 206 such that second induction coil 304 is disposed radially surrounding (relative to axis 404) first induction coil 302.

Additionally, first induction coil 302 and second induction coil 304 may be hermetically sealed and/or encased so as to prevent fluids from directly contacting first induction coil 302 and/or second induction coil 304 when implanted in a patient. For example, as shown, first induction coil 302 may be encased in a protective layer 406 and second induction coil 304 may be encased in a protective layer 408. Protective layer 406 and protective layer 408 may each comprise a substantially impermeable polymer, such as epoxy, that encases and surrounds the wires forming first induction coil 302 and second induction coil 304. In some examples, a separate protective layer, such as a hermetic enclosure, may surround first induction coil 302 and/or second induction coil 304.

When implantable battery module 126 passes an electric current through second induction coil 304, a magnetic field may be generated around second induction coil 304. First induction coil 302 may be positioned and oriented such that the magnetic field generated by second induction coil 304 at least partially surrounds first induction coil 302. The magnetic field surrounding second induction coil 304 may thus generate a corresponding current in first induction coil 302. The current generated in first induction coil 302 may be transferred to cochlear implant circuitry 112 of cochlear implant module 110. Accordingly, power may be transferred via first induction coil 302 and second induction coil 304 from implantable battery module 126 to cochlear implant circuitry 112, without requiring direct electrical contact between first induction coil 302 and second induction coil 304. Additionally, because power is inductively transferred between first induction coil 302 and second induction coil 304, first induction coil 302 and second induction coil 304 may be hermetically sealed off from each other and from the internal bodily environment of the patient, thereby preventing leakage of current into the patient and/or preventing degradation of components of first connector assembly 202 and second connector assembly 204. The electrically conductive components of first connector assembly 202 and second connector assembly 204 are protected from body fluids even in situations where body fluids migrate between first connector assembly 202 and second connector assembly 204 (e.g., in a region within receptacle 206).

In some examples, cochlear implant circuitry 112 may be configured to detect that first connector assembly 202 is connected to second connector assembly 204. When first connector assembly 202 and second connector assembly 204 are connected one to another, implantable battery module 126 may begin transferring power to cochlear implant circuitry 112. Implantable battery module 126 may comprise circuitry for modulating a power signal transferred via connector junction 122 to cochlear implant circuitry 112. Likewise, cochlear implant circuitry 112 may be configured to demodulate the modulated power signal transferred by implantable battery module 126. First connector assembly 202 and second connector assembly 204 may be arranged in various configurations where at least one of first connector assembly 202 and second connector assembly 204 surrounds the other of first connector assembly 202 and second connector assembly 204.

Figure 5:
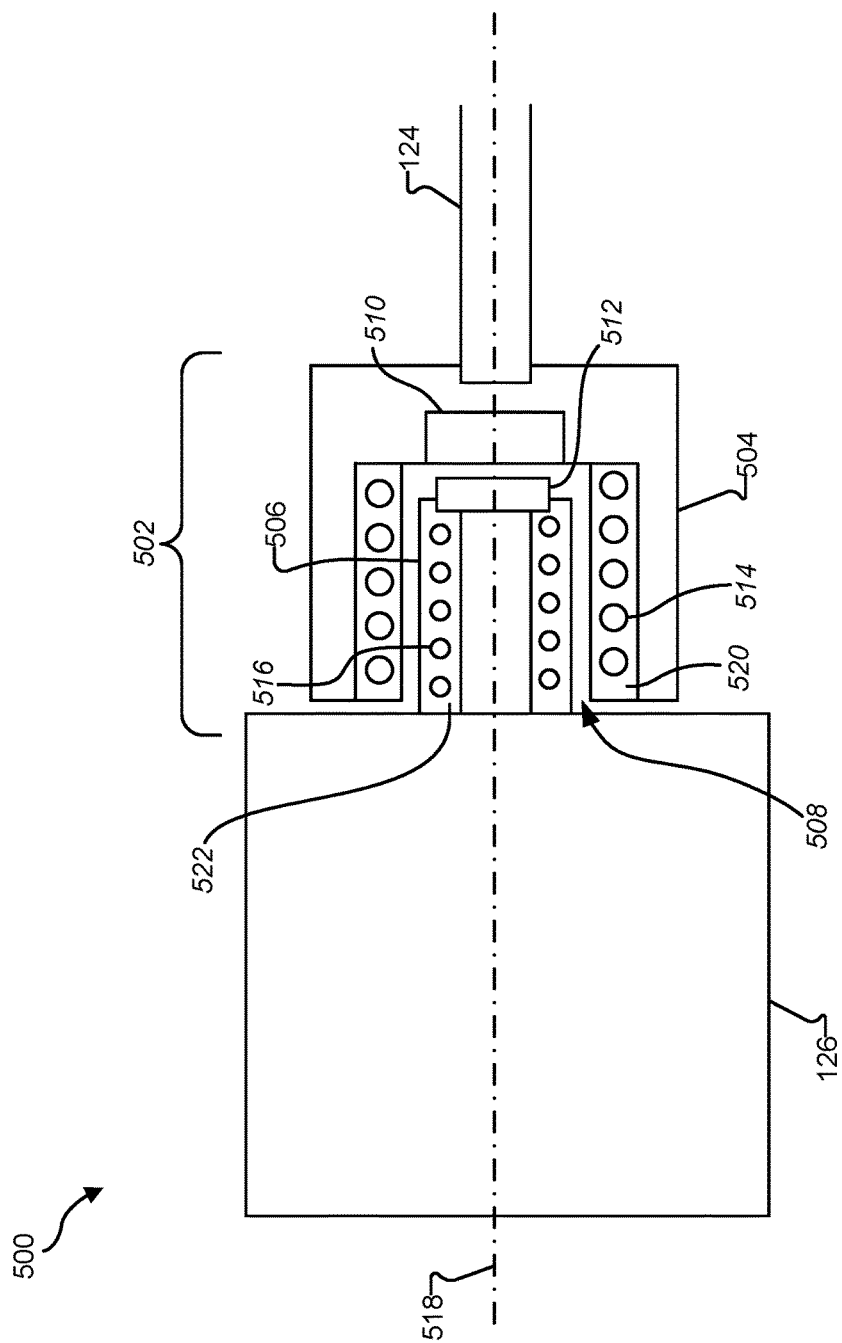

FIG. 5 shows another exemplary configuration 500 of connectorized cochlear implant system 100 in which a connector junction 502 includes a first connector assembly 504 that is connected to a second connector assembly 506. As shown, first connector assembly 504 may have a receptacle 508 in which second connector assembly 506 is disposed. First connector assembly 504 may comprise a magnet 510, or other fastening component, that is configured to be disposed adjacent magnet 512 of second connector assembly 506, or other suitable fastening component, thereby securing first connector assembly 504 to second connector assembly 506.

First connector assembly 504 may comprise a first induction coil 514 and second connector assembly 506 may comprise a second induction coil 516. First connector assembly 504 and second connector assembly 506 may both be formed so as to surround an axis 518. As shown, first induction coil 514 of first connector assembly 504 may be positioned radially surrounding second induction coil 516 of second connector assembly 506 (relative to axis 518). Additionally, first induction coil 514 and second induction coil 516 may be hermetically sealed and/or encased. For example, first induction coil 514 may be encased in a protective layer 520 and second induction coil 516 may be encased in a protective layer 522. In some examples a connector assembly may be located closer to cochlear implant module 110.

Figure 6:
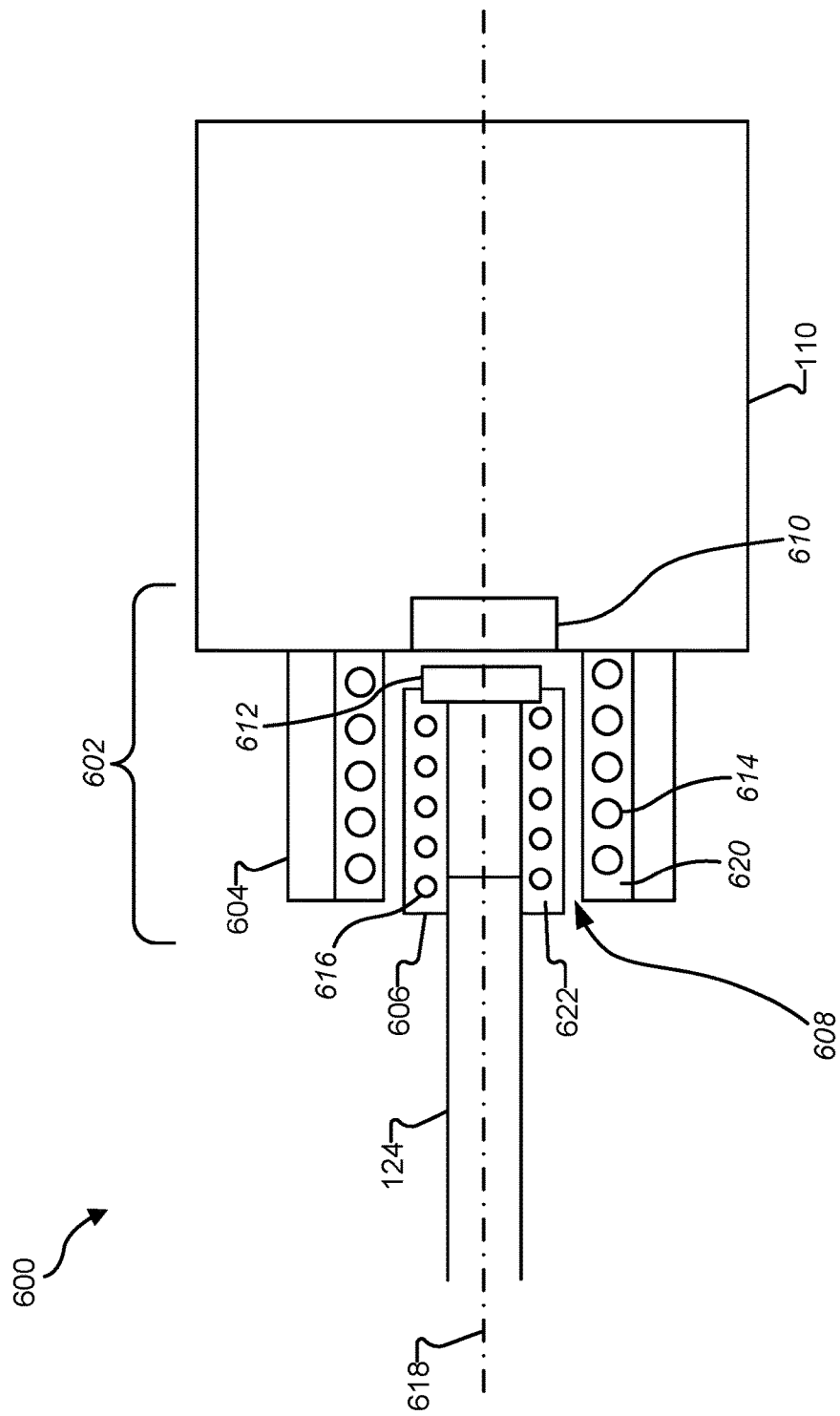

To illustrate, FIG. 6 shows another exemplary configuration 600 of connectorized cochlear implant system 100 in which a connector junction 602 includes a first connector assembly 604 that is connected to a second connector assembly 606. As shown, first connector assembly 604 may be disposed on cochlear implant module 110 and may include a receptacle 608 in which second connector assembly 606 is disposed. Connector assembly 604 may comprise a magnet 610, or other fastening component, that is configured to be disposed adjacent magnet 612, or other suitable fastening component, of second connector assembly 606, thereby securing first connector assembly 604 to second connector assembly 606.

First connector assembly 604 may comprise a first induction coil 614 and second connector assembly 606 may comprise a second induction coil 616. First connector assembly 604 and second connector assembly 606 may both be formed so as to surround an axis 618. As shown, first induction coil 614 of first connector assembly 604 may be positioned radially surrounding second induction coil 616 of second connector assembly 606 (relative to axis 618). Additionally, first induction coil 614 and second induction coil 616 may be hermetically sealed and/or encased. For example, first induction coil 614 may be encased in a protective layer 620 and second induction coil 616 may be encased in a protective layer 622. In some examples, both connector assemblies of a connector junction may be attached to electrical cables as opposed to being directly disposed on either of implantable battery module 126 or cochlear implant module 110.

Figure 7:
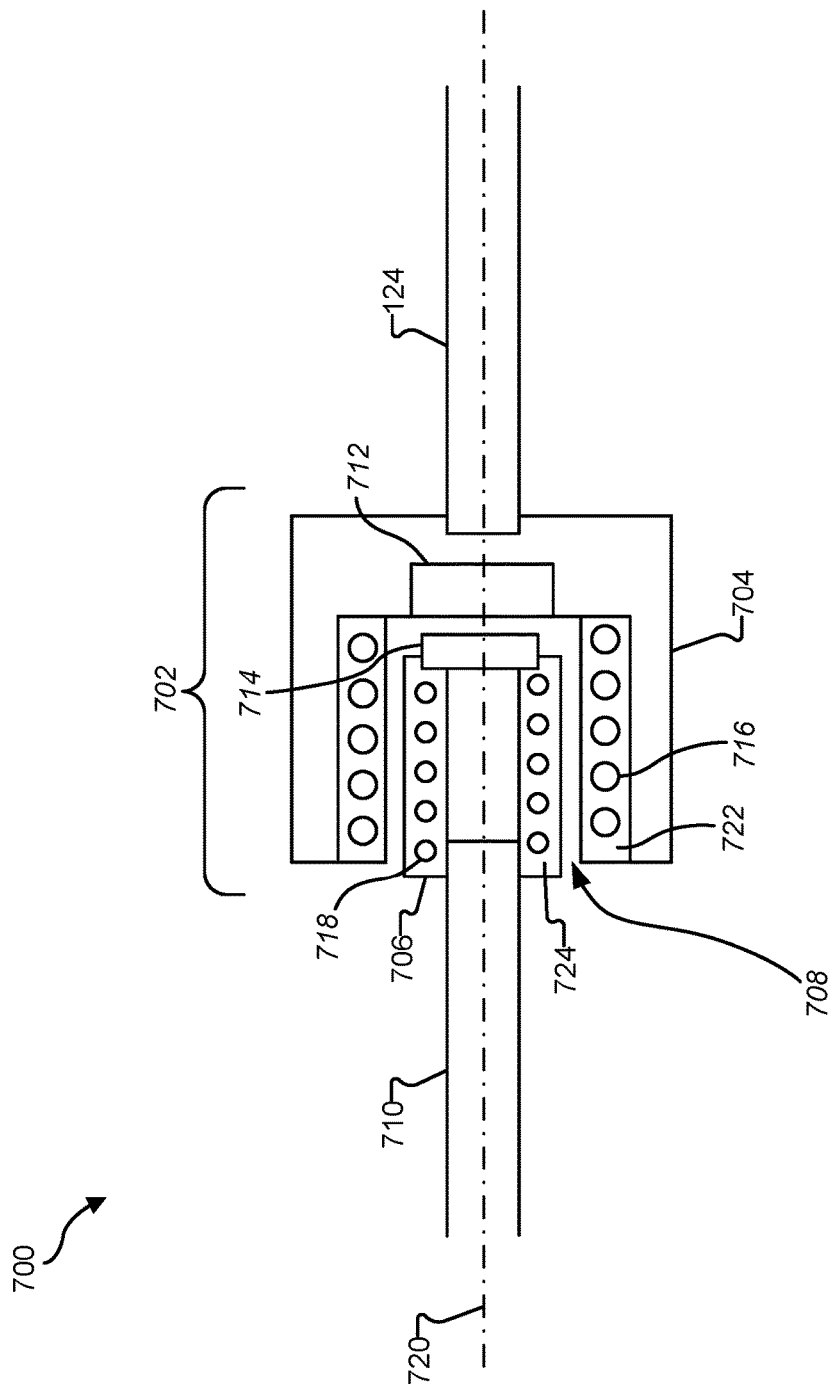

For example, FIG. 7 shows another exemplary configuration 700 of connectorized cochlear implant system 100 in which a connector junction 702 includes a first connector assembly 704 that is connected to a second connector assembly 706. As shown, first connector assembly 704 may be attached to cable 124 at a location between cochlear implant module 110 and implantable battery module 126. Additionally, second connector assembly 706 may be attached to cable 710 at a location between cochlear implant module 110 and implantable battery module 126. First connector assembly 704 may include a receptacle 708 in which second connector assembly 706 is disposed. First connector assembly 704 may comprise a magnet 712, or other fastening component, that is configured to be disposed adjacent magnet 714, or other suitable fastening component, of second connector assembly 706, thereby securing first connector assembly 704 to second connector assembly 706.

First connector assembly 704 may comprise a first induction coil 716 and second connector assembly 706 may comprise a second induction coil 718. First connector assembly 704 and second connector assembly 706 may both be formed so as to surround an axis 720. As shown, first induction coil 716 of first connector assembly 704 may be positioned surrounding second induction coil 718 of second connector assembly 706 (relative to axis 720). Additionally, first induction coil 716 and second induction coil 718 may be hermetically sealed and/or encased. For example, first induction coil 716 may be encased in a protective layer 722 and second induction coil 718 may be encased in a protective layer 724. In some examples, in addition to transferring power signals from implantable battery module 126, a connector junction comprising connector assemblies having inductive coils may also inductively transfer data signals to cochlear implant circuitry 112 of cochlear implant module 110.

Figure 8:
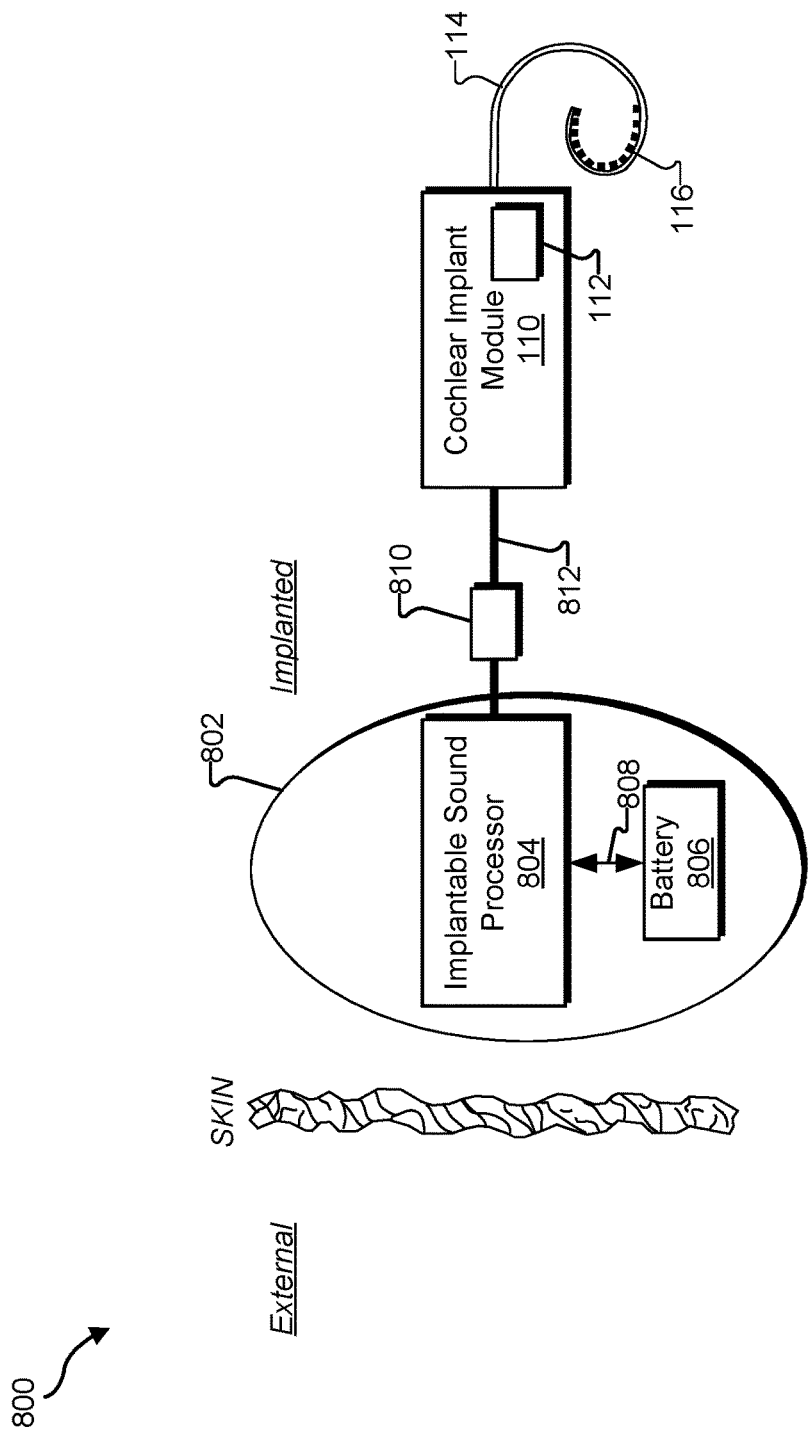

FIG. 8 alternatively illustrates another exemplary configuration 800 of connectorized cochlear implant system 100 in which an implantable module comprises a single overmold 802 (or other type of hermetic housing) that houses both an implantable sound processor 804 and an implantable battery 806. In this implementation, a connector junction 810 may be located between implantable sound processor 804 and cochlear implant module 110. Connector junction 810 may be coupled to cochlear implant module 110 by way of cable 812. Both power signals from implantable battery 806 and data signals from implantable sound processor 804 may be inductively transferred via connector junction 810 to cochlear implant circuitry 112 of cochlear implant module 110.

Figure 9:
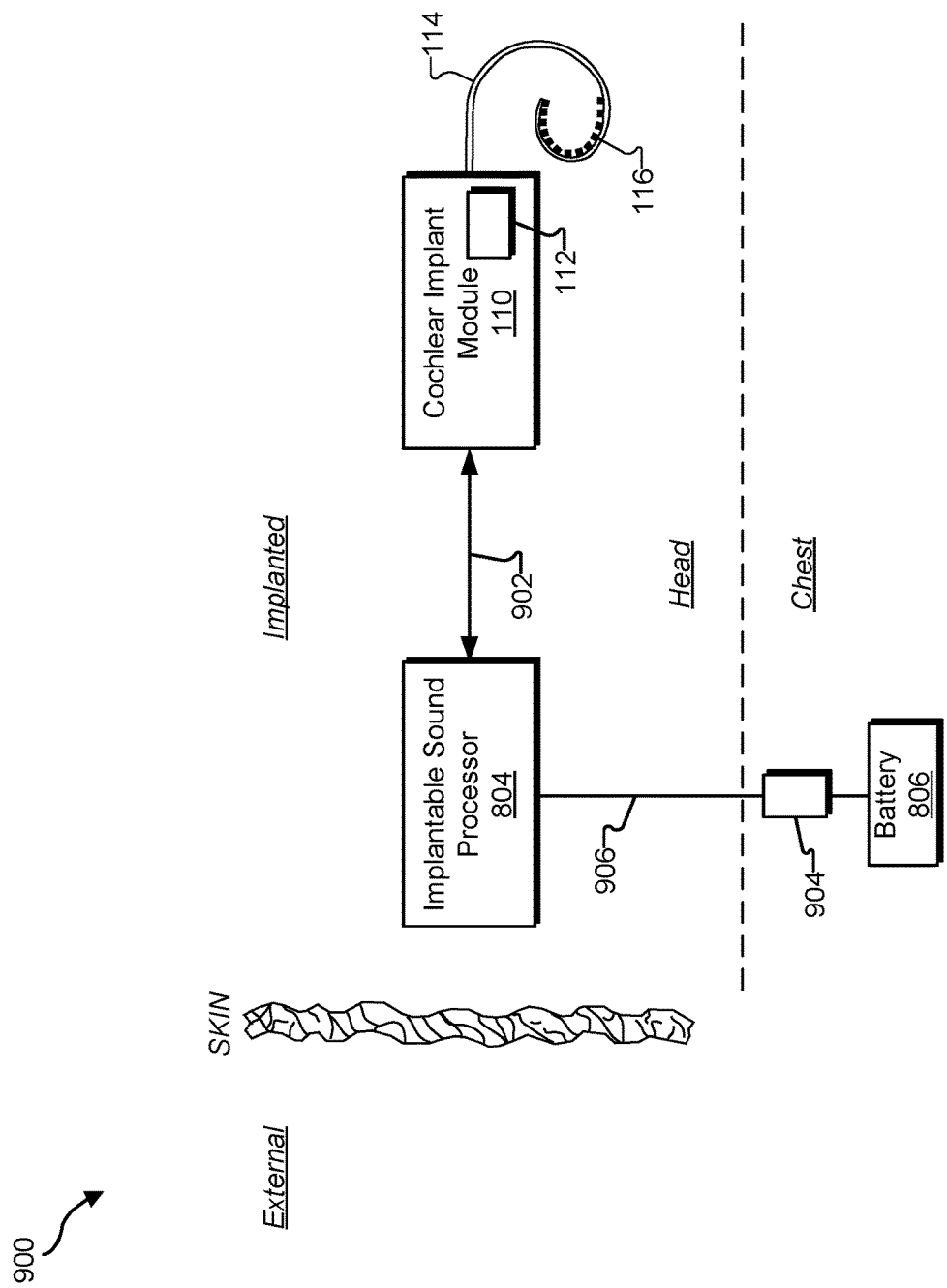

In some examples, both implantable sound processor 804 and implantable battery 806 are implanted within the head of the patient. Alternatively, as shown in the exemplary implementation 900 of FIG. 9, implantable sound processor 804 may be implanted within the head of the patient and implantable battery 806 may be implanted within the chest of the patient (or in any other suitable location capable of being implanted with a relatively large battery). In this case, communication link 902 may be implemented by a cable and/or one or wires extending from implantable sound processor 804 to cochlear implant module 110. In some examples, a connector junction 904 may be located between implantable battery 806 and implantable sound processor 804. Connector junction 904 may be coupled to implantable sound processor 804 by way of cable 906 and may facilitate transfer of power from battery 806 to implantable sound processor 804.

Additional or alternative connector junctions similar to those described herein may be included in a cochlear implant system. For example, one or more connector junctions may be used to connect cochlear implant module 110 to lead 114, cochlear implant module 110 to an implantable antenna, and/or cochlear implant module 110 to any other component as may serve a particular implementation.

In some examples, the connector assemblies included in a connector junction may each include multiple sets of induction coils. For example, a first connector assembly included in a connector junction may include two or more induction coils located side by side. These induction coils may be positioned in a manner that allows them to be inductively coupled to corresponding induction coils included in a second connector assembly of the connector junction. Alternatively, the induction coils included in the first connector assembly may be stacked (e.g., disposed along a protruding member, such as a pin). In this embodiment, the second connector assembly may include a corresponding receptacle configured to receive the protruding member. Induction coils may be disposed within the second connector assembly in a manner that allows them to be inductively coupled to the induction coils of the first connector assembly when the protruding member is inserted into the receptacle.

By including multiple induction coils in each connector assembly, a multi-channel inductive link may be realized. This multi-channel inductive link may be used to separate the transfer of power from the transfer of data between two components, realize simultaneous bi-directional communication between two components, drive a plurality of independent electrode contacts, and/or in any other manner as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a cochlear implant module configured to be implanted within a patient and comprising cochlear implant circuitry configured to apply electrical stimulation representative of one or more audio signals to the patient; and
    a first connector assembly coupled to the cochlear implant module and configured to be implanted within the patient, the first connector assembly comprising a first set of induction coils and a first magnet;
    wherein
        the first connector assembly is further configured to be removably connected to a second connector assembly comprising a second set of induction coils and a second magnet and coupled to an implantable module in order to facilitate transfer of power between the implantable module and the cochlear implant module via the first and second sets of induction coils,
        the first and second magnets form a magnetic connection therebetween while the first connector assembly is connected to the second connector assembly, the magnetic connection configured to secure the connection between the first and second connector assemblies, and
        while the first connector assembly is connected to the second connector assembly
            the first and second sets of induction coils are configured to form a multi-channel inductive link between the implantable module and the cochlear implant module,
            each induction coil included in the first set of induction coils surrounds a common axis with a corresponding induction coil included in the second set of induction coils, and
            either each induction coil included in the first set of induction coils radially surrounds a corresponding induction coil included in the second set of induction coils or each induction coil included in the second set of induction coils radially surrounds a corresponding induction coil included in the first set of induction coils.

2. The system of claim 1, wherein the multi-channel inductive link is configured to separate a transfer of power between the implantable module and the cochlear implant module from a transfer of data between the implantable module and the cochlear implant module.

3. The system of claim 1, wherein the multi-channel inductive link is configured to realize simultaneous bi-directional communication between the implantable module and the cochlear implant module.

4. The system of claim 1, wherein the multi-channel inductive link is configured to drive a plurality of independent electrode contacts communicatively coupled to the cochlear implant module.

5. The system of claim 1, wherein the first connector assembly further comprises a substantially hermetic enclosure surrounding each induction coil included in the first set of induction coils.

6. The system of claim 1, wherein the first connector assembly further comprises a locking member configured to secure the first connector assembly to the second connector assembly.

7. The system of claim 1, wherein the cochlear implant circuitry is further configured to:
    detect that the first connector assembly is connected to the second connector assembly;
    receive a power signal from the implantable module while the first connector assembly is connected to the second connector assembly; and
    demodulate the power signal.

8. The system of claim 1, wherein the first connector assembly is coupled to the cochlear implant module by way of a cable.

9. A system comprising:
    a cochlear implant module configured to be implanted within a patient and comprising cochlear implant circuitry configured to apply electrical stimulation representative of one or more audio signals to the patient;
    a first connector assembly coupled to the cochlear implant module and configured to be implanted within the patient, the first connector assembly comprising a first set of induction coils and a first magnet;
    an implantable module configured to be implanted within the patient; and
    a second connector assembly coupled to the implantable module and configured to be implanted within the patient, the second connector assembly comprising a second set of induction coils and a second magnet;
    wherein
        the first connector assembly is configured to be removably connected to the second connector assembly in order to facilitate inductive transfer of power between the first and second sets of induction coils,
        the first and second magnets form a magnetic connection therebetween while the first connector assembly is connected to the second connector assembly, the magnetic connection configured to secure the connection between the first and second connector assemblies, and
        while the first connector assembly is connected to the second connector assembly
            the first and second sets of induction coils are configured to form a multi-channel inductive link between the implantable module and the cochlear implant module,
            each induction coil included in the first set of induction coils surrounds a common axis with a corresponding induction coil included in the second set of induction coils, and
            either each induction coil included in the first set of induction coils radially surrounds a corresponding induction coil included in the second set of induction coils or each induction coil included in the second set of induction coils radially surrounds a corresponding induction coil included in the first set of induction coils.

10. The system of claim 9, wherein the multi-channel inductive link is configured to separate a transfer of power between the implantable module and the cochlear implant module from a transfer of data between the implantable module and the cochlear implant module.

11. The system of claim 9, wherein the multi-channel inductive link is configured to realize simultaneous bi-directional communication between the implantable module and the cochlear implant module.

12. The system of claim 9, wherein the multi-channel inductive link is configured to drive a plurality of independent electrode contacts communicatively coupled to the cochlear implant module.

13. The system of claim 9, wherein the implantable module comprises an implantable battery.

14. The system of claim 9, wherein the implantable module comprises an implantable sound processor.

15. The system of claim 9, wherein the first set of induction coils does not physically contact the second set of induction coils while the first connector assembly is connected to the second connector assembly.

16. The system of claim 9, wherein the first connector assembly is mechanically fastened to the second connector assembly while the first connector assembly is connected to the second connector assembly.

17. A system comprising:
an implantable module configured to be implanted with a patient and configured to transfer power to a cochlear implant module; and
a first connector assembly coupled to the implantable module and configured to be implanted within the patient, the first connector assembly comprising a first set of induction coils and a first magnet;
wherein
the first connector assembly is further configured to be removably connected to a second connector assembly comprising a second set of induction coils and a second magnet and coupled to the cochlear implant module in order to facilitate transfer of power between the implantable module and the cochlear implant module via the first and second sets of induction coils,
the first and second magnets form a magnetic connection therebetween while the first connector assembly is connected to the second connector assembly, the magnetic connection configured to secure the connection between the first and second connector assemblies, and
while the first connector assembly is connected to the second connector assembly
the first and second sets of induction coils are configured to form a multi-channel inductive link between the implantable module and the cochlear implant module,
each induction coil included in the first set of induction coils surrounds a common axis with a corresponding induction coil included in the second set of induction coils, and
either each induction coil included in the first set of induction coils radially surrounds a corresponding induction coil included in the second set of induction coils or each induction coil included in the second set of induction coils radially surrounds a corresponding induction coil included in the first set of induction coils.

18. The system of claim 17, wherein the multi-channel inductive link is configured to separate a transfer of power between the implantable module and the cochlear implant module from a transfer of data between the implantable module and the cochlear implant module.

19. The system of claim 17, wherein the multi-channel inductive link is configured to realize simultaneous bi-directional communication between the implantable module and the cochlear implant module.

20. The system of claim 17, wherein the multi-channel inductive link is configured to drive a plurality of independent electrode contacts communicatively coupled to the cochlear implant module.

* * * * *